(12) United States Patent
Dehmer

(10) Patent No.: US 7,036,526 B1
(45) Date of Patent: May 2, 2006

(54) VALVE FOR LIQUID SEPARATION

(75) Inventor: Bernhard Dehmer, Rastatt (DE)

(73) Assignee: Agilent Technologies, Inc., Palo Alto, CA (US)

( * ) Notice: Subject to any disclaimer, the term of this patent is extended or adjusted under 35 U.S.C. 154(b) by 909 days.

(21) Appl. No.: 09/672,038

(22) Filed: Sep. 29, 2000

(30) Foreign Application Priority Data

Sep. 29, 1999 (DE) .................................. 199 46 654

(51) Int. Cl.
*F16K 11/044* (2006.01)
(52) U.S. Cl. ..................................... 137/625.5; 137/901
(58) Field of Classification Search ............ 137/625.5, 137/625.48, 901; 251/359
See application file for complete search history.

(56) References Cited

U.S. PATENT DOCUMENTS

| 1,937,246 | A | * | 11/1933 | Reedy | ................. | 137/625.5 X |
| 2,542,390 | A | * | 2/1951 | Brown | ................. | 137/625.48 |
| 3,461,911 | A | * | 8/1969 | Janczur | ................. | 137/625.5 |
| 4,262,697 | A | * | 4/1981 | Davis | ................. | 137/625.5 |

FOREIGN PATENT DOCUMENTS

| DE | 35 02 588 | | 4/1987 |
| DE | 37 44 026 | | 7/1988 |
| DE | 37 90 818 | | 10/1989 |
| DE | 195 09 145 | | 9/1996 |
| EP | 0 274 781 | * | 7/1988 |
| EP | 0 679 821 | | 11/1995 |
| EP | 0 907 045 | | 4/1999 |
| SU | 0 593 038 | * | 2/1978 |

* cited by examiner

Primary Examiner—John Fox

(57) ABSTRACT

A valve for liquid separation, especially for analytical or preparative liquid chromatography, includes a valve body having an inlet and at least two outlets connected to the inlet for a flow of liquid. The valve body includes a sealing element having shut-off surfaces for alternately shutting off the outlets. The shut-off surfaces face away from each other and have the shape of a cone segment or spherical segment.

12 Claims, 1 Drawing Sheet

VALVE FOR LIQUID SEPARATION

Figure 1:
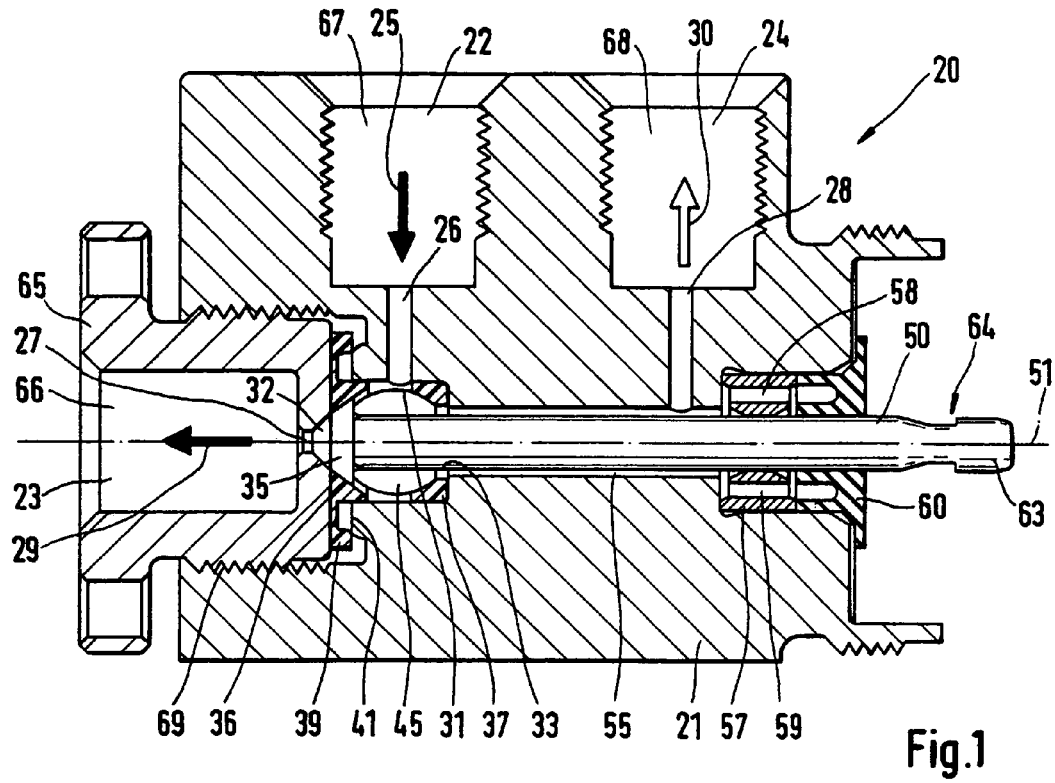

The invention concerns a valve for liquid separation, especially for analytical or preparative high performance liquid chromatography, with a valve body that has an inlet and at least two outlets that can be connected to the inlet in which a shutter element with shut-off surfaces can be used to alternately shut off the outlets directly by means of conical or spherical segment shut-off surfaces.

Samples separated by means of liquid separation, e.g. analytical or preparative liquid chromatography, must be transported or collected in a suitable manner. Important criteria for the system and separating parameters are an optimum resolution per unit time, or a high flow rate of the substance to be isolated at a given purity. This is measured by means of suitable detectors. To separately collect the respective fractions, detector-controlled valves are used to divert into suitable receptacles the liquid flow leaving the analytical column.

To this end, there is a series of prior-art valves that, however, all have certain disadvantages. A first decisive disadvantage is that a significant band widening can occur due to the valve construction, i.e., the desired separation does not occur. This can be due to problematic channel path and design, and especially due to poor design of the valve chambers, for example from dead zones such as blind holes or cavities that are poorly flushed, or by the internal valve volume. Some of the fraction can creep into these areas and mix with following fractions. In addition, substantial pressure peaks can sometimes arise when the valves are switched when the channels are briefly closed and/or when there are changes in volume when switching. These pressure peaks can lead to corresponding signal distortion in the chromatogram of the detectors used to control the valves, whereby an incorrect trigger pulse can be induced for the switching time of the valves. This can have a catastrophic effect on the quality of the fractions to be collected. Other disadvantages can arise in conjunction with the large construction-related forces that arise during switching and/or large forces that arise to ensure a sufficient seal when the valves are in the shut-off position. Large and strong drives are therefore necessary which run counter to the need for a very small installation space.

Finally, depending on the respective valve constructions, the valves can unintendedly open due to the counterpressure on the outlet side, and essential parts that form the valve can be prematurely destroyed.

A switch valve for liquid separation that has become known as a membrane valve and has the above-cited features includes a valve body with an inlet channel that ends in a ring channel that is perpendicular to the inlet channel. The ring channel can be selectively sealed by one of two opposing shut-off cones whose rod-shaped extensions run in the center of the ring channel, and the extensions contact each other for force transmission. The conical surfaces of the two shut-off cones oppose each other and are arranged so that they can seal the outlets of the ring channel designed as valve seats. The two shut-off cones are connected at the cone base to a membrane that is perpendicular to the ring channel and parallel to the inlet channel. These flexible membranes seal the liquid chambers connected to the outlets of the ring channel, whereby the liquid chambers connect with the actual outlet channels.

With this construction, there are particularly problematic blind-hole-like areas in the ring channel and in the liquid chambers assigned to the membrane. In these areas that have a poor or non-existent flow, the described remixing effects can occur with corresponding band widening.

With this double cone construction, liquid pressure that forms in the ring channel acts against the sealing force that is necessary to press one of the valve cones against the valve seat to seal one of the outlets. This requires correspondingly large holding and switching forces, hence this construction requires relatively large drive units.

In addition, a relatively large volume is displaced when switching the valves due to the membrane. This can make the valves sluggish. Furthermore, undesirable pressure peaks can arise that influence the detector signals so that the valves do not precisely switch which can produce undesirable band widening.

Another disadvantage of this construction is that membranes can be strongly stressed when pressure increases on the outlet side. This can lead to early membrane failure and, when the outlet channel is sealed, to the immediate destruction of the membranes.

It is therefore the problem of the invention to create a valve for liquid separation, especially for analytical or preparative liquid chromatography that avoids the disadvantages of the above-described state of the art.

This problem is solved by the features of patent claim 1, particularly in that the shut-off surfaces assigned to the outlet openings face away from each other.

By means of these relatively simple measures, a valve for liquid separation can be created where the danger of band widening is reduced to a minimum by advantageous flushing. Another advantage of a valve designed in this manner is that the liquid pressure acting on the outlet side increases the sealing force, and the switching stroke is short with less volume displacement. In particular, small pulse drives can be used that enable frequent, precise and quick valve switching over a long time. When this valve is switched, undesirable pressure peaks do not arise that can affect the detectors via the inlet channel. By means of these measures, the purity of the collected fractions can be increased, and such valves are distinguished by a particularly long life.

The shut-off surfaces are usefully connected radially and symmetrically to an actuation axis of an actuator connected to the sealing element, preferably designed as a valve lifter. This favorably self-centers and hence positively seals the sealing element and produces a favorable bearing and seal of the actuator so that the essential valve parts operate reliably over a long time.

The sealing element is advantageously on the free end of the actuator. This produces a particularly favorable design of the valve body surrounding the sealing element and accordingly of the liquid-conducting cavities in view of the particularly favorable rinsing behavior that minimizes band widening.

Advantageously, the cross-section of the shut-off surfaces and the parts of the surface of the sealing elements opposite the inlet opening essentially form a continuous line. The liquid flow is hence favorably guided and diverted without the formation of dead zones, and the sealing elements can be manufactured easily and precisely.

When one of the outlets is shut off, the sealing element with its shut-off surfaces assigned to this outlet advantageously lies on the opposing shut-off surfaces of a valve seat of the valve body and forms an annular sealing surface. This provides a good seal while the sealing element is centered on the valve seat, and it favorably guides the flow when open.

The opposing shut-off surfaces at the annular sealing surface advantageously form an angle with the actuation axis of the actuator that is greater or equal to 15°, and preferably greater than or equal to 30°. These angles advantageously center the element without the danger of the sealing element locking to the valve seat.

The opposing shut-off surfaces of the valve seat usefully consist of a softer and elastic material, preferably Teflon, in contrast to the shut-off surface of the sealing elements. This produces particularly favorable friction and sealing conditions, and the valve parts are inert to the used liquids.

It is advantageous for the opposing shut-off surfaces at the sealing surface to have a step or nose-like projection. This allows the shut-off surfaces of the sealing element to quickly reach a precise sealing position with a self-sealing effect under liquid pressure.

The opposing shut-off surface of the valve body that preferably faces the free end of the actuator narrows toward the outlet as a cone or funnel. This produces particularly good flushing behavior of the internal hydraulic volume. This does a particularly good job of diverting the useful fraction into the primary channel.

The outlets on both sides of the inlet are advantageously opposite each other. This provides an advantageous seal with short flow paths without substantial pressure peaks when the valve is switched.

Both individually and together, the above measures contribute to the purity of the collected fractions without substantial band widening and without pressure peaks when the valve is switched; in addition, the drive units are small, the switching forces are low, and the valve has a long life.

Other features, aspects and advantages of the invention can be found in the following description with reference to the figures.

Figure 2:
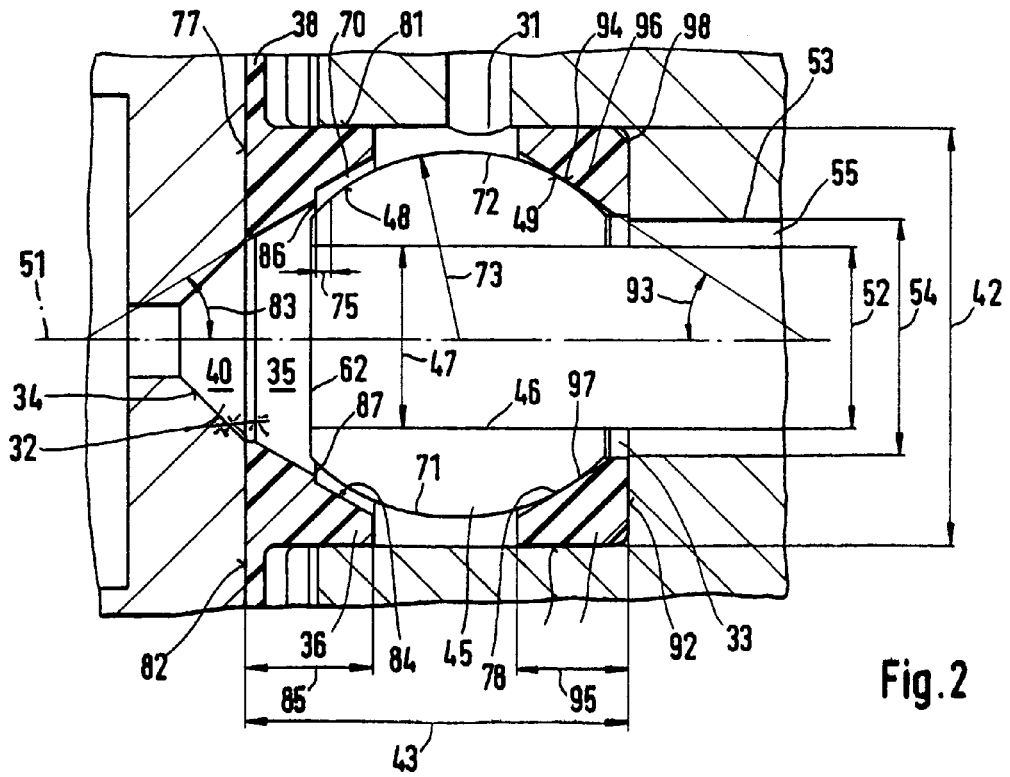

A preferred exemplary embodiment of the invention will be described in the following with reference to the figures. Shown are:

FIG. 1 is a cross-sectional view of a valve for liquid separation according to a preferred embodiment of the invention; and FIG. 2 is an enlarged cross-section of the valve body with the sealing element inside of the valve illustrated in FIG. 1.

The valve 20 in FIG. 1 is designed as a three/two-way valve and has a valve body 21 with external inlet 22 and a primary external outlet 23 and secondary external outlet 24. Inlet 22 has a connecting hole 67 to connect connecting lines (not shown) and ends in the cylindrical inlet channel 26. Channel 26 ends in interior inlet 31 that is assigned to the switching chamber 35. The switching chamber 35 also has a primary interior outlet 32 and secondary interior outlet 33 that is opposite the primary interior outlet 32. The interior outlets 32, 33 are symmetrical to the actuation, i.e., longitudinal axis 51 of actuator 50 and are on opposite sides of the inlet 31 at an angle of 90° to the interior inlet.

In the switching chamber 35 is first annular valve seat 36 assigned to the primary interior outlet 32 and the second annular valve seat 37 assigned to the secondary interior outlet 33. Also in the switching chamber 35 is the switchable sealing element 45 that is shaped as a segment of a sphere and can move in the direction of the actuation axis 51 and is rotatably mounted around the actuation axis 51. Sealing element 45 is between the first annular valve seat 36 and the second annular valve seat 37. The end of sealing element 45 closest to outlet port 32 is tapered toward port 32 and axis 51, while the opposite end of sealing element 45 (that is closest to outlet port 33) is tapered toward port 33 and axis 51. The spherical sealing element 45 is affixed to the actuator designed as a tappet valve 50 that is guided through channel 55 having an interior end connected to the secondary outlet 33. The tappet valve 50 is mounted and guided in the radial bearing 57, and its actuating end 63 has a fastener 64 that can be coupled to an actuating drive (not shown). The actuating drive preferably includes a directional pulse generator or a spring-loaded retention magnet with an active and passive switching state, or a similar actuator.

The radial bearing 57 has holes 58, 59 through which the liquid in cylindrical channel 55 can pass. Contacting the radial bearing 57 is a radial seal 60 that has suitably designed ring lip zones so the seal performs a self-sealing function under liquid pressure.

The primary interior outlet 32 of the switching chamber 35 communicates with the primary outlet channel 27 of the ring flange 65 including connecting hole 66 of the primary exterior outlet 23 to which suitable connecting lines can be connected. The connecting flange 65 can be screwed into and out of the threaded hole 69 in valve body 21, and its sealing inner surface 77, perpendicular to the actuation axis 51, abuts contact surface 82 of the first annular valve seat 36. As can be seen in particular in FIG. 1, the entire valve 20 is easy to mount, adjust and remove. This allows the entire valve 20 with its essential valve parts to be quickly and easily cleaned.

Each of valve seats 36 and 37 included in switching chamber 35 has a cylindrical exterior surface that is coaxial with axis 51 and has a diameter indicated by reference numeral 42; the combined lengths of valve seats 36 and 37 and the space between them has a length indicated by reference numeral 43 in the direction of axis 51. The dimensions and volume of the switching chamber 35 are adapted to the valve parts inside it, that is, the first annular valve seat 36, the second annular valve seat 37, and the sealing element 45. Sealing element 45 is attached to the free end 62 of the tappet valve 50 to yield a short switching stroke having a length in the direction of axis 51 indicated by reference numeral 75. Hence, when sealing element 45 is actuated completely to the right (as indicated in FIGS. 1 and 2) there is a low volume displacement between inlet 31 and outlet 32. The liquid volume displaced when the valve 20 switches and the surface projection that determines the switching force are small enough to yield short switching times with short drives.

The first annular valve seat 36 including outlet 32 has a cylindrical surface 81 that is co-axial with axis 51. Seat 36 has an outer diameter that corresponds to the inner diameter 42 of the cylindrical switching chamber 35. In addition, the first annular valve seat 36 has a contact surface 82 that is perpendicular to the cylindrical surface 81. Surface 82 continues radially outward to form the ring flange 38 of valve seat 36 that has an outer ring 39 on the outer edge. The first annular valve seat 36 is received by the contact ring 41 of the valve body 21 in a force fit and positive fit. The valve seat 36 also has first and second segments respectively including frusto-conical surfaces 80 and 84 which are coaxial and displaced along axis 51. Each of surfaces 80 and 84 has a constant slope that extends along a straight line away from outlet port 32 and axis 51 by an angle; the angle between axis 51 and surface 80 is indicated by reference number 83. Surfaces 80 and 84 together have a length in the direction of axis 51 that is slightly less than the length of valve seat 36, indicated by reference numeral 85. The radii of the end of surface 80 farthest from port 32 and the end of surface 84 closest to port 32 differ slightly from each other by virtue of the radius of the end of surface 80 farthest from port 32 being slightly less than the radius of the end of surface 84 closest to port 32. These end surfaces are substantially aligned in the direction of axis 51. The spacing between surfaces 80 and 84 in the radial direction at right angles to axis 51 thus has a step or nose-shaped projection 86 that forms annular sealing lip 87. Lip 87 forms a sealing surface with the periphery of sealing element 45 when the sealing element is translated from the first position thereof illustrated in FIGS. 1 and 2 to the initial contact of the element with lip 87.

To provide a fluid flow path from inlet channel 26 to outlet channel 28 when sealing element 45 is shifted along axis 51 to the left from the position illustrated in FIGS. 1 and 2, passage 55 is provided between the inlet and outlet channels. Passage 55 has an annular cross section formed between the outer diameter of the rod forming actuator 50 and the inner diameter of the central opening in housing 21 that extends in the direction of axis 51.

The second cylindrical annular valve seat 37 is radially delimited by a cylindrical surface 91 whose outer diameter corresponds to the diameter indicated by reference numeral 42 of the cylindrical switching chamber 35. The second annular valve seat 37 also has a contact surface 92 that is perpendicular to the cylindrical surface 91; surface 92 abuts the ring step 98 of the valve body 21. The second annular valve seat 37 also has a second opposing frusto-conical shut-off surface 94 having a constant inclination angle 93 that extends away from actuation axis 51. The second opposing shut-off surface 94 includes step or nose-shaped projection 96 that forms annular sealing lip 97. Surface 94 extends along the length of axis 51 by a distance that is slightly less than the length of valve 37, which is indicated by reference numeral 95.

The angle indicated by reference numeral 83 of the first opposing shut-off surface 84 and the angle indicated by reference numeral 93 of the second opposing shut-off surface 94 are approximately 30 degrees in the preferred embodiment to provide a favorable, centered and slightly sealing contact for the sealing element 45 without the sealing element 45 locking at annular sealing surface 78 of seat 37 while the first and second annular valve seats 36, 37 are sealed.

The inner diameter of the first annular valve seat 36 transitions toward the actuation axis 51 from the inner radius of surface 84 into the frusto-conical narrowing opening surface 34 of the primary outlet 32. This forms an outlet area 40 with a particularly favorable flow that is delimited by the first opposing shut-off surface 84 and the annular opening surface 34. The inner diameter of the second annular valve seat 37 is the same or slightly bigger than the diameter 54 of hole 53 so that the design of this area is also favorable to flow.

The sealing element 45 between the two valve seats 36 and 37 includes a spherical segment with a radius indicated by reference numeral 73 and a regular cylindrical hole 46 having an axis coincident with axis 51. Prior to element 45 being installed, hole 46 has an inner diameter 47 slightly smaller than the outer diameter 52 of the cylindrical tappet valve 50 so that a tight press seat of the sealing element 45 on the tappet valve 50 results when element 45 is installed. The sealing element 45 has a first shut-off surface 48 that faces a first opposing shut-off surface 84 of valve seat 36, and a second shut-off surface 49 facing the second opposing shut-off surface 94 of valve seat 36. Due to the spherical shape of sealing element 45, the first shut-off surface 48 and second shut-off surface 49 face away from each other relative to the center diameter of the sealing element that is at right angle to longitudinal axis 51. In a cross section at right angles to longitudinal axis 51, first shut-off surface 48 and second shut-off surface 49 lie along an arc defined by the radius of the spherical portion of sealing element 45. Hence the exterior portion of sealing element 45 extends along an essentially continuous spherical surface 72 between centrally located inlet 31 and the first and second opposed shut-off surfaces 84, 94.

The sealing element 45 preferably consists of high-grade steel while the first and the second annular valve seats 36 and 37 preferably consist of softer, elastic teflon. The contact and seal are therefore favorable, and the teflon is inert to the liquids of the collected fractions.

The functioning of the valve 20 is as follows:

In the first position, as shown in FIGS. 1 and 2, second shut-off surface 49 of sealing element 45 seals against the second opposing shut-off surface 94 of the second annular valve seat 37 to seal the secondary outlet 33. In this position, a narrow annular gap 70 is formed between the first shut-off surface 48 of sealing element 45 and the opposing shut-off surfaces 80 and 84 of the first annular valve seat 36. An optimized flow of liquid passes through gap 70 following the arrow 25 through the inlet channel 26 and inlet 31 into the switching chamber 35 of the valve body 21 to fill the part of the switching chamber 35 assigned to the interior primary outlet 32 and the outlet chamber 40. The liquid can leave the primary outlet chamber 40 in the direction of the arrow 29. In this manner, the liquid can be collected in a suitable receptacle during a first interval assigned to the first fraction, preferably the useful fraction of the liquid.

As soon as the drive unit (controlled by an upstream detector (not shown) before the valve 20) rapidly switches the valve 20, the tappet valve 50 bearing the sealing element 45 is shifted transversely to channel 26, i.e., along axis 51, in the direction of the arrow 29. The sealing element 45 moves in the direction of the arrow 29 until its first shut-off surface 48 seals the step or nose-shaped projection 86 between surfaces 80 and 84, designed as a sealing lip 87. In the brief transition period in which the first shut-off surface 48 has not yet reached the projection 86 between surfaces 80 and 84, neither the primary outlet 32 nor the secondary outlet 33 is sealed by the sealing element 45. This prevents the formation of pressure peaks.

When the sealing element 45 contacts the sealing lip 87, the pressurized liquid entering the inlet channel 26 and interior inlet 31 of switching chamber 35 and leaving through channel 55 independently and additionally presses the first shut-off surface 48 of the sealing element 45 against the opposing shut-off surface 80 of the first annular valve seat 36 so that the thus formed liquid pressure effectively supports the sealing force. The projection 86, shaped as a sealing lip 87 between surface 84 and opposing shut-off surface 80, deforms slightly so that there is a sufficiently wide annular sealing surface available to form a seal.

In this switched state (not shown in FIGS. 1 and 2) in which the sealing element 45 is pressed against the first annular valve seat 36, the liquid of the second fraction entering in the direction of the arrow 25, preferably consisting of the eluents, passes through the annular channel 55. The arrangement and design of the inlet channel 26 of the sealing element 45, second annular valve seat 37 and switching chamber 35 produce a swirling flow of liquid. This causes the liquid to advantageously and completely circulate around the tappet valve 50 and through annular channel 55. The second fraction then flows through the second outlet channel 28 (arrow 30) and is available at the second exterior outlet 24 with the connecting hole 68 to be collected in a suitable receptacle.

Numerous additional switching operations can follow corresponding to the described steps.

In the preferred embodiment of FIGS. 1 and 2, valve 20 has an asymmetrical liquid path that is designed for optimum flow and circulation (arrows 25 and 29). This is also attained by placing interior inlet 31 directly next to the second annular valve seat 37 so that the narrow sealing gap between the second shut-off surface 49 of sealing element 45 and the second opposing shut-off surface 94 of the second annular valve seat 37 are optimally flushed. This effect can be increased by angling or tilting the inlet channel 26 so that the direction of the flow induced through the channel 26 forms an acute angle with the actuation axis 51. The flushing and outflowing effect can be further enhanced by angling the inlet channel 26 eccentric to the actuation axis 51 so that the flow formed through the inlet channel 26 runs at a distance from the actuation axis 51 so that the liquid flow through the inlet 31 into the switching chamber 35 swirls around the axis 51.

Of course, beyond the free end 62 of the tappet value 50, the sealing element 45 can also be located in the area of a part of the tappet value 50 shifted toward the actuating end 51 so that an annular channel corresponding to annular channel 55 can be formed on opposite sides of the sealing elements 45. In addition, there can also be several sealing elements 45 affixed to the single tappet value 50 they are offset axially toward the actuation axis 51, and several additional inlet and outlet channels can be correspondingly created. This allows several liquid-containing channels to be advantageously switched simulataneously.

I claim:

1. A valve for liquid separation comprising a valve body having an inlet and at least first and second outlets on opposite sides of the inlet, and a sealing element for closing, at different times, flow from the inlet to the first outlet and from the inlet to the second outlet, the sealing element including first and second shut-off surfaces for respectively shutting off the first and second outlets, both of the first and second shut-off surfaces including an arcuate segment, the first and second shut-off surfaces being arranged to face away from each other and being at a free end of an actuator, the valve body having third and fourth shut-off surfaces respectively associated with the first and second outlets, the third and fourth shut-off surfaces respectively being engaged by the first and second sealing surfaces when the first and second sealing surfaces respectively close the first and second outlets at different times, portions of the third and fourth shut-off surfaces respectively in closest proximity to the first and second outlets narrowing conically or as a funnel toward the first and second outlets, an outlet area being arranged between the third shut-off surface and the first outlet, the outlet area having a conically narrowing opening surface.

2. The valve of claim 1, wherein the first, second, third and fourth shut-off surfaces are radially symmetrical to an actuation axis of the actuator for translating the sealing element.

3. The valve of claim 2, wherein the actuator includes a tappet valve connected to the sealing element.

4. The valve of claim 3, wherein the first and second shut-off surfaces are connected to each other and arranged so each cross-section of the first and second surfaces as connected together in planes extending in the direction of longitudinal movement of the actuator forms an essentially continuous arcuate line.

5. The valve of claim 1, wherein the first and second outlets and sealing element are arranged so that when the first outlet is shut off, the first shut-off surface rests on the third shut-off surface to form an annular seal.

6. The valve of claim 1, wherein the first shut-off surface forms an angle with the actuation axis at the annular sealing surface that is greater than or equal to 15°.

7. The valve of claim 6, wherein the angle is at least 30°.

8. The valve of claim 1, wherein the third and fourth shut-off surfaces are formed of material that is softer and more elastic than the first and second shut-off surfaces.

9. The valve of claim 8, wherein the material of the third and fourth surfaces is TEFLON.

10. The valve of claim 1, wherein the third shut-off surface has a step-shaped projection or a nose-shaped projection at one of the locations where the first and third surfaces intersect to form an annular seal.

11. The valve of claim 1, wherein the outlets oppose each other.

12. The valve of claim 1, wherein the third shut-off surface has a step-shaped projection or nose-shaped projection at an annular seal between the first and third surfaces when the first outlet is closed.

* * * * *